US009232964B2

(12) United States Patent
Freudiger et al.

(10) Patent No.: US 9,232,964 B2
(45) Date of Patent: Jan. 12, 2016

(54) SPINAL IMPLANT SET FOR THE DYNAMIC STABILIZATION OF THE SPINE

(75) Inventors: Stefan Freudiger, Bremgarten (CH); Rolf Diener, Winkel (CH)

(73) Assignee: SPINESAVE AG (CH)

( * ) Notice: Subject to any disclaimer, the term of this patent is extended or adjusted under 35 U.S.C. 154(b) by 148 days.

(21) Appl. No.: 13/817,866

(22) PCT Filed: Aug. 23, 2011

(86) PCT No.: PCT/CH2011/000192
§ 371 (c)(1),
(2), (4) Date: Feb. 20, 2013

(87) PCT Pub. No.: WO2012/024807
PCT Pub. Date: Mar. 1, 2012

(65) Prior Publication Data
US 2013/0158606 A1 Jun. 20, 2013

(30) Foreign Application Priority Data

Aug. 26, 2010 (CH) ...................................... 1379/10

(51) Int. Cl.
*A61B 17/70* (2006.01)
(52) U.S. Cl.
CPC ............ *A61B 17/7001* (2013.01); *A61B 17/701* (2013.01); *A61B 17/7004* (2013.01); *A61B 17/7011* (2013.01); *A61B 17/7026* (2013.01); *A61B 17/7031* (2013.01); *A61B 17/7032* (2013.01); *A61B 17/7034* (2013.01)
(58) Field of Classification Search
CPC ........... A61B 17/7031; A61B 17/7001; A61B 17/7004; A61B 17/701; A61B 17/7032; A61B 17/7034

USPC .......................................... 606/254–265, 270
See application file for complete search history.

(56) References Cited

U.S. PATENT DOCUMENTS

| 5,217,461 | A | 6/1993 | Asher et al. |
| 7,326,210 | B2 | 2/2008 | Jahng et al. |
| 7,815,663 | B2 | 10/2010 | Trieu |
| 2005/0203513 | A1 | 9/2005 | Jahng et al. |
| 2008/0177320 | A1 | 7/2008 | McBride |
| 2009/0118767 | A1 | 5/2009 | Hestad et al. |
| 2009/0248083 | A1 | 10/2009 | Patterson et al. |
| 2010/0010542 | A1 | 1/2010 | Jackson |
| 2010/0114165 | A1 | 5/2010 | Ely |

FOREIGN PATENT DOCUMENTS

| EP | 2 047 812 | 4/2009 |
| WO | WO 97/32533 | 9/1997 |
| WO | WO 2007/038429 | 4/2007 |
| WO | WO 2007/087476 | 8/2007 |
| WO | WO 2007/089957 A1 | 8/2007 |
| WO | WO 2009/021116 | 2/2009 |
| WO | WO 2011/006267 | 1/2011 |

OTHER PUBLICATIONS

International Search Report and Written Opinion dated Oct. 6, 2011 issued in corresponding International patent application No. PCT/CH2011/000192.

*Primary Examiner* — Ellen C Hammond
(74) *Attorney, Agent, or Firm* — Ostrolenk Faber LLP

(57) ABSTRACT

A connection element (1) for stabilizing vertebral bodies that has a variable stiffness along its longitudinal axis in that particularly the cross-section of the connecting element varies along its longitudinal axis and extends over a plurality of bone screws (6). In spite of the varying cross-section (h1, h2), in a preferred embodiment, the same bone screws (6) may be used in all locations by inserting clamping elements (9, 10) of different lengths.

16 Claims, 3 Drawing Sheets

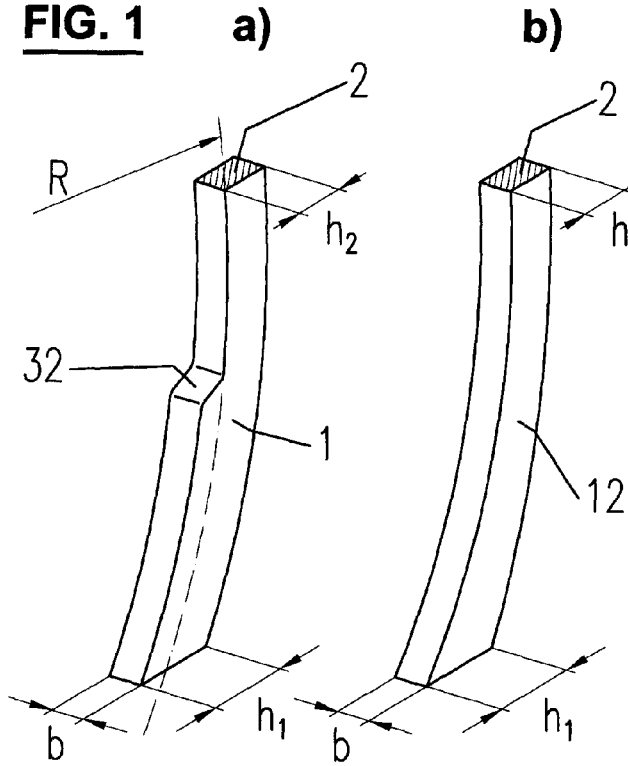
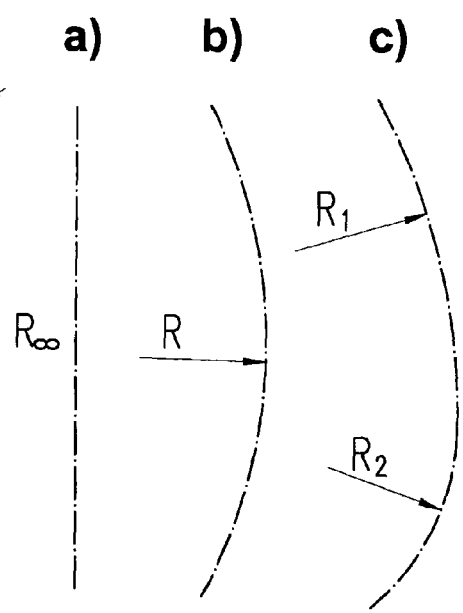
FIG. 1
FIG. 2
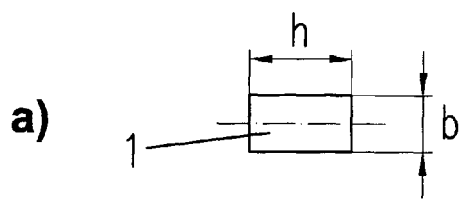
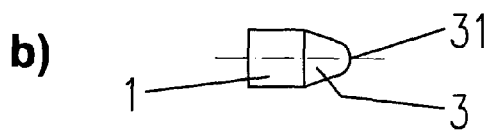
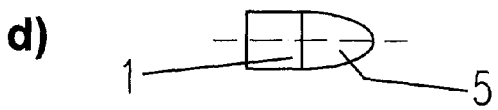
FIG. 3 a)

b)

c)

b)

SPINAL IMPLANT SET FOR THE DYNAMIC STABILIZATION OF THE SPINE

CROSS REFERENCE TO RELATED APPLICATIONS

The present application is a 35 U.S.C. §371 National Phase conversion of PCT/CH201/000192, filed Aug. 23, 2011, which claims benefit of Swiss Application No. 1379/10, filed Aug. 26, 2010, the disclosure of which is incorporated herein by reference. The PCT International Application was published in the English language.

BACKGROUND OF THE INVENTION

The present invention relates to a spinal implant set for the dynamic stabilization of the spine according to the preamble of claim 1 and a use thereof.

The present invention allows to realize an elastic connecting rod having different degrees of stiffness along its longitudinal axis and usable for dynamically stabilizing vertebral bodies. Elastic connecting rods are typically used in conjunction with bone screws (pedicle screws) for the dynamic stabilization of the spine. If such a rod is provided with a section of higher stiffness, the possible indications can be substantially extended. Thus, a section of higher stiffness may e.g. be used for the fusion of a vertebral body while a section of lower stiffness may be used for the elastic connection of a neighboring segment.

The "golden standard" in spinal surgery today still consists in the fusion (stiffening) of pathologic vertebral bodies. However, the stiffening often leads to premature degeneration of the segments adjacent to the fusion. Therefore, attempts are being made to provide rods having different degrees of stiffness and to include the neighboring segments in the surgical treatment.

As shown below, the approaches that are known in the art relate to combinations of metal and plastic rods, on one hand, and to plastics rods having variable cross-sections, on the other hand.

The invention according to patent application EP 1 719 468 connects a metal bar to a textile band that is intended to act as an inner traction structure in an outer plastic cushion to form a connected dynamic stabilization.

The invention according to patent specification EP 1 815 812 provides, at the end of a metal rod, a part for receiving a connectable plastic rod.

The invention according to patent application US 2009/0118767 shows a connecting element having variable flexibility along its longitudinal axis. Here the variable flexibility is limited to the area between two anchoring elements, and only the outer body of the connecting element is varied in its stiffness.

The invention according to patent application US 2009/0248083 shows connecting rods having areas of different stiffness along their longitudinal axis which only extend over one motion segment, however, i.e. act between two consecutive fastening screws.

The invention according to patent application WO 97/32533 shows (rigid) connecting rods varying in diameter along their longitudinal axis, which is however limited to the area between two fastening screws.

The invention according to patent application WO 2007/038429 shows a stack of load-bearing elements that should be stiff in the longitudinal direction and elastic in the transversal direction. However, the intended difference in stiffness is only achieved between two respective fastening screws.

The invention according to patent application US 2005/0203513 aims to achieve different degrees of stiffness between respective motion segments or pairs of fastening screws. However, the suggested solution provides no continuous variation over the respective fastening screws so that the connecting element necessarily requires predetermined graduations of the fastening locations, which may result in considerable difficulties for the surgeon in multisegmental applications.

The invention according to patent application US 2007/0191832 suggests a plurality of bodies having different degrees of elasticity between at most two fastening screws and is therefore limited to at most unisegmental treatments.

The invention according to patent application WO 2007/087476 provides different degrees of stiffness between two fastening screws in that the connecting rods have a longitudinal cavity and different external contours. However, the variable cross-sections are limited to unisegmental treatments and due to the cavities are barely suitable for anchoring e.g. elastic rods in bone screws.

The invention according to patent U.S. Pat. No. 7,326,210 suggests connecting elements having elastic areas between the fastening screws that are either suitable for unisegmental applications only or necessarily subject to the problem of the predetermined graduation.

The invention according to patent application WO 2007/089957 also describes variable cross-sections along the rod axis, however in predetermined segments, which requires an individually adapted rod with corresponding segment lengths for each patient. The flattened sides of the rod are orthogonal to the axis of a potential bone screw. Connections of the rod to the bone are not shown.

The invention according to patent application WO 2009/021116 describes variable cross-sections along the rod axis, too, however only between the fastening screws, therefore again requiring a particular rod with corresponding segment lengths for each patient. The suggested dynamic rod system seems not to be suitable for fusions, i.e. for predominantly compressive forces. Furthermore it is doubtful whether the combination of fibers over a molded core can withstand several millions of load cycles without degradation.

The invention according to patent application EP-A-2047812 describes variable cross-sections along the rod axis, however only between the fastening screws, which is again linked to the problem of predetermined segment lengths. Furthermore, the rod is made of metal and cannot be considered as a dynamic fixation system, neither isolated nor on a transitional segment.

The invention according to patent application US 2010/0114165 shows a round rod having a variable cross-section along the rod axis in that the radius decreases in the cranial direction. However, at the cranial end, the rod is not firmly connected to the vertebral body, especially not by using the same bone screws as used further caudally. The invention according to patent specification U.S. Pat. No. 5,217,461 also describes two different diameters of the connecting rod along the rod axis, but does not specify how these different rods are connected to the spine, and even less that one single type bone screw can be used therefore.

SUMMARY OF THE INVENTION

Accordingly, it is an object of the present invention to provide a spinal implant set comprising a rod of varying stiffness usable in a more extended range of orthopedic situations.

Such a spinal implant set is defined in claim 1. The further claims define preferred embodiments and a use of the implant set.

The implant set according to the invention comprises a connection element or rod the stiffness of which varies over at least two neighboring areas along its longitudinal axis but which is not subject to the disadvantages of a predetermined graduation.

This is accomplished in that the cross-section varies continuously or in at least one step, preferably exactly one step, along the rod axis, preferably in such a manner that the same bone screws with the same seats can be used for the entire connection element.

Preferably, the spinal implant set according to the invention comprises a connecting element having a cross-sectional variation that extends over at least three bone screws.

The present invention is explained in more detail hereinafter by way of preferred embodiments with reference to drawings which do not show all possibilities of varying cross-sections along a rod axis.

BRIEF DESCRIPTION OF THE DRAWINGS

The figures schematically show:

FIG. 1 pre-bent rectangular rods having different cross-sections along the longitudinal axis of the rod;

FIG. 2 a straight and two pre-bent longitudinal axes of rods;

FIG. 3 different nose shapes of the rod cross-section in a top view;

DESCRIPTION OF PREFERRED EMBODIMENTS

Figure 4:
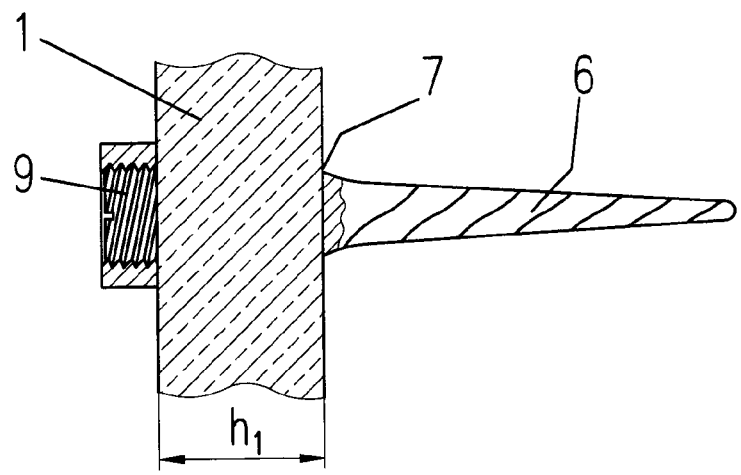
FIG. 4 partial longitudinal sections of different screw heads and clamping elements for receiving the rod of varying cross-section.
Figure 4:
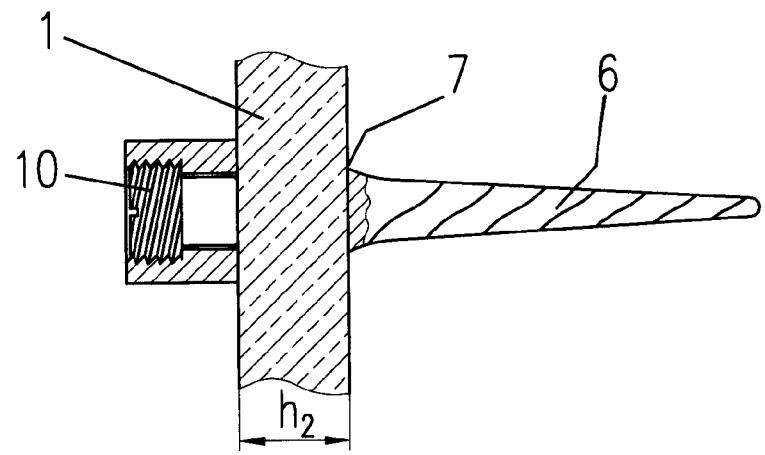
Figure 4:
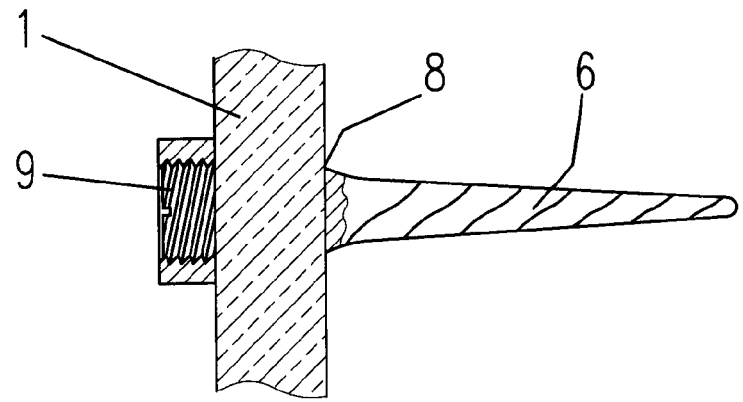

An implant set for the dynamic fixation of the spine has been described in the earlier patent application WO 2011/6267 of the applicant. The disclosure of that patent application is incorporated by reference and in particular describes the preferred fastening system for fastening the connection element of the spine implant set to bone screws. More particularly, a spinal implant comprises a connection rod which has two opposite, plane-parallel faces of which one dimension extends in the direction of insertion in a seat of a bone screw. As explained in WO 2011/6267, this feature allows to circumferentially clamp the rod in a hydrostatic in-plane manner, i.e. the clamping pressure exerted on the whole clamping contour. Thereby, flowing of the rod material in the clamping plane is avoided, and namely rods of polymeric material are therefore held in a long time stable fashion.

In FIG. 1 a pre-bent connection element or rod 1, 12 is depicted whose rectangular cross-section 2 varies in one dimension (h1, h2), preferably in the direction of the curvature radius (R), along the rod axis. FIG. 1a shows a rod 1 wherein the variation is stepwise. Preferably, only one step 32 is present. FIG. 1b shows a rod 12 with a continuous variation of the cross section.

In FIG. 2 a straight longitudinal rod axis, one that is pre-bent according to a radius (R), and one that is bent according to two different radii (R1, R2) are depicted.

In FIG. 3a the rod 1 has no particular nose shape.

In FIG. 3b the rod 1 has a triangular nose shape 3 with a rounded apex 31.

In FIG. 3c the rod 1 has a semicircular nose shape 4.

In FIG. 3d the rod 1 has a semi-elliptical nose shape 5. The nose shapes according to FIGS. 3b to 3d facilitate the insertion of the rod 1 in the seat 7 of the bone screw 6 as explained in WO 2011/6267.

In FIG. 4a a bone screw 6 having a large seat 7 for a large rod cross-section h1 and a short clamping element 9 are depicted.

In FIG. 4b a bone screw 6 having a large seat 7 for a small rod cross-section h2 and a long clamping element 10 are depicted.

In FIG. 4c a bone screw 6 having a small seat 8 for a small rod cross-section h2 and a short clamping element 9 are depicted.

Figure 5:
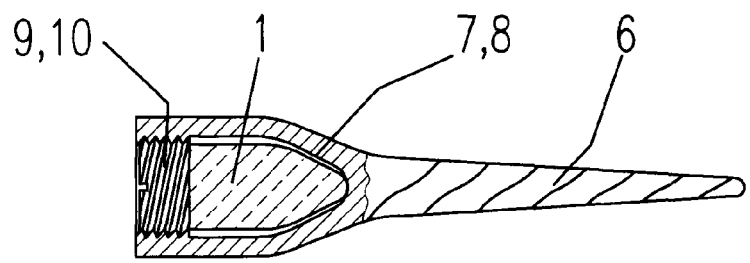
FIG. 5 partial cross-sections of two versions of a rod with a clamping element in the seat of the bone screw.

FIG. 5a shows a top view of a rod 1 with a clamping element 9, 10 in the form of a headless screw, in the seat 7, 8 of the bone screw 6.

FIG. 5b shows a top view of a rod 1 with a clamping element 9, 10 in the form of a spacer with an additional external nut 11 in the seat 7, 8 of the bone screw (6). The nut engages in an exterior thread in the head of bone screw 6.

Figure 6:
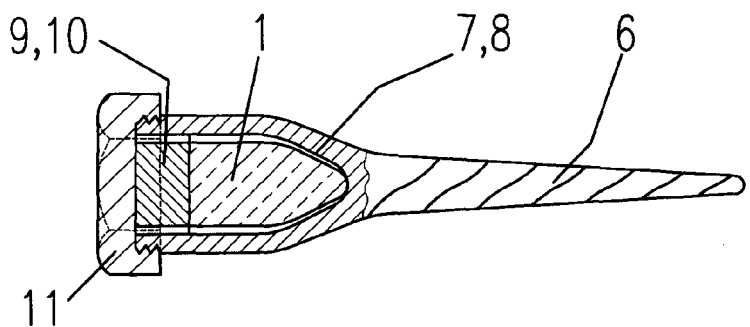
FIG. 6 schematized illustration of a pre-bent rod having different cross-sections along the rod axis that is received in a plurality of bone screws of the same type.
Figure 6:
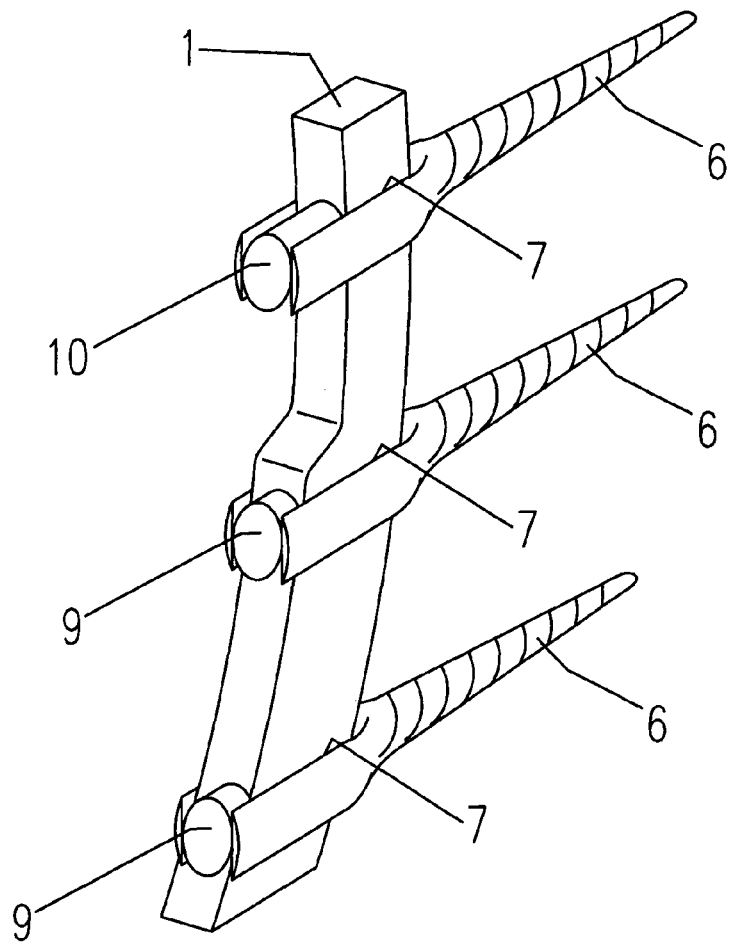

In FIG. 6 a pre-bent rod 1 whose cross-section varies along the rod axis is depicted that is secured in three bone screws 6 of the same type having three identical seats 7 with two short 9 and one long clamping element 10. The bone screws may e.g. be those of WO 2011/6267, yet with clamping elements of varying dimensions.

To realize the invention, countless combinations of embodiments may be contemplated. A few preferred embodiments will be non-exhaustively explained here. The rod cross-section may be rectangular with plane-parallel sides, e.g. according to WO-A-2011/6267. The cross-section may vary along the longitudinal axis of the rod while its height (h), its width (b), or both are varied. The rod may be supplied as a straight rod (R=∞ (infinite)) or as a pre-bent rod with one or multiple different curvature radii (R1, R2). In the case of a rectangular rod cross-section, one or more sides, preferably at the forward side as seen in the direction of the bone screw 6, may be provided with a particular nose shape. This nose shape may e.g. (cf. FIG. 3) be triangular 3 with a rounded apex 31, semi-circular 4, or semi-elliptical 5. The nose shape may be attached or integrated (in one piece).

In the case of cross-sections that vary in the direction of the screw axis, the same bone screws may be used along the rod axis and clamping elements of merely different lengths are applied. The advantage of bone screws of the same type is that during revision surgery (e.g. extension surgery) screws that are well integrated into the bone may be preserved and sections of merely different rod stiffness can be inserted.

A preferred material for such connecting elements is PCU (polycarbonate-urethane) since it is available in different degrees of stiffness or elasticity, respectively, and has an excellent biocompatibility and outstanding mechanical long-term behavior. However, other polymers may also be contemplated, e.g. those of the PEEK family (polyetheretherketones).

Preferably (cf. FIG. 6), a first or forward side of the connecting rod may follow a line, whereas the opposite or rearward side may be stepped with respect to the first side. The first side will be pushed first in the seats of the bone screws. The continuous shape of the forward side complies with the anatomical situation. Only the spacers or other clamping means pressed on the rearward side of the connection rod need to be chosen to compensate the differing heights, or—more generally—dimensions, of the connection rods.

However, even the first side may be shaped unevenly, e.g. stepped, and spacers may be inserted as necessary between the bottom of the seat in the bone screw and the connection rod.

What is claimed is:

1. A spinal implant set for dynamic stabilization of a spine, the spinal implant set comprising:
   two or more bone screws; and
   at least one elongated connection element having a cross section varying along a longitudinal axis of the elongated connection element,
   wherein the cross section has two plane-parallel side faces extending in a direction of insertion of a bone screw, and a rearward side and a forward side, the rearward side and the forward side lying transverse to the direction of the insertion,
   wherein the variation of the cross section is substantially accomplished by the variation of a distance between the rearward side and the forward side,
   wherein the cross section variation is accomplished exclusively by at least one step comprised in the rearward side of the elongated connection element, and
   wherein the forward side to be arranged in the seat of the bone screws toward the bone thread of the bone screw extends along a straight or curved line.

2. The spinal implant set of claim 1, wherein said elongated connection element is straight.

3. The spinal implant set of claim 1, wherein the varying cross section of the elongated connection element comprises a portion of constant cross section along the direction of the longitudinal axis such that the portion is insertable in at least two bone screws when implanted.

4. The spinal implant set of claim 1, wherein the forward side of the elongated connection element comprises a rounded nose portion.

5. The spinal implant set of claim 4, wherein the cross-section of the rounded nose portion of the elongated connection element substantially consists of a triangle with a rounded apex.

6. The spinal implant set of claim 4, wherein the cross-section of the rounded nose portion of the elongated connection element substantially consists of a semi-circle.

7. The spinal implant set of claim 4, wherein the cross-section of the rounded nose portion of the elongated connection element substantially consists of a semi-ellipse.

8. The spinal implant set of claim 1, wherein the two or more bone screws comprise:
   a first bone screw comprising a seat for the elongated connection element;
   a second bone screw comprising a seat for the elongated connection element,
   wherein the seat of the first bone screw is substantially identical to the seat for the elongated connection element of the second bone screw; and
   the first bone screw comprises a first clamping insert insertable in the seat of the first bone screw; and
   the second bone screw comprises a second clamping insert configured to be inserted in the seat of the second bone screw, such that the first and second clamping inserts compensate for the differing heights of the connection element.

9. The spinal implant set of claim 1, wherein a reduced cross section portion is at at least one end of the elongated connection element.

10. The spinal implant set of claim 1, wherein the elongated connection element is made of a plastic material.

11. The spinal implant set of claim 10, wherein the plastic material is polycarbonate-urethane (PCU).

12. The spinal implant set of claim 10, wherein the plastic material is of the family of polyetheretherketone (PEEK).

13. The spinal implant set of claim 1, wherein the variation of the cross section of the elongated connection element comprises at least one step.

14. The spinal implant set of claim 1, wherein said elongated connection element is pre-bent with at least one radius.

15. The method of claim 1, wherein the at least one step comprises exactly one step.

16. The method of claim 1, wherein the at least one step comprises exactly two steps.

* * * * *